United States Patent
Ye et al.

(10) Patent No.: US 9,572,790 B2
(45) Date of Patent: *Feb. 21, 2017

(54) TRANSMUCOSAL TAXANE COMPOSITION

(71) Applicant: LP PHARMACEUTICAL (XIAMEN) CO., LTD., Xiamen (CN)

(72) Inventors: Ying Ye, Irvine, CA (US); Janshon Zhu, San Diego, CA (US)

(73) Assignee: XIAMEN LP PHARMACEUTICAL CO., LTD., Xiamen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/690,289

(22) Filed: Apr. 17, 2015

(65) Prior Publication Data

US 2015/0297554 A1    Oct. 22, 2015

Related U.S. Application Data

(63) Continuation of application No. 13/604,487, filed on Sep. 5, 2012, now Pat. No. 9,018,246.

(51) Int. Cl.
| | |
|---|---|
| *A61K 31/337* | (2006.01) |
| *A61K 9/00* | (2006.01) |
| *A61K 9/08* | (2006.01) |
| *A61K 47/10* | (2006.01) |
| *A61K 47/26* | (2006.01) |
| *A61K 47/32* | (2006.01) |

(52) U.S. Cl.
CPC ............ *A61K 31/337* (2013.01); *A61K 9/006* (2013.01); *A61K 9/08* (2013.01); *A61K 47/10* (2013.01); *A61K 47/26* (2013.01); *A61K 47/32* (2013.01)

(58) Field of Classification Search
CPC .................. A61K 31/37; A61K 9/003
See application file for complete search history.

(56) References Cited

U.S. PATENT DOCUMENTS

| | | | |
|---|---|---|---|
| 2006/0104999 | A1 | 5/2006 | Chung et al. |
| 2007/0190544 | A1 | 8/2007 | Giannakakou et al. |
| 2011/0190204 | A1 | 8/2011 | Head et al. |

FOREIGN PATENT DOCUMENTS

| | | |
|---|---|---|
| CN | 101227893 A | 7/2008 |
| CN | 101829061 A | 9/2010 |
| WO | WO 2010/023321 A1 | 3/2010 |
| WO | WO 2011/063421 A1 | 5/2011 |

OTHER PUBLICATIONS

International Search Report and Written Opinion of International Application No. PCT/CN2013/082989 with a mailing date of Dec. 12, 2013.
Liu et al.; "Advances in the Study of Delivery of Taxol"; Tianjin Chemical Industry; vol. 17, No. 3, pp. 41-43 (May 2003)—w/ English translation of abstract.
"Progress in Clinical Studies of Taxol in Antitumor"; Journal of Binzhou Vocational College; vol. 5, No. 3, pp. 24-27 (Aug. 2008)— w/ English translation of abstract.
Shojaei, A.H. "Buccal Mucosa As A Route for Systemic Drug Delivery: A Review" J. Pharm. Pharmaceut. Sci., 1998, vol. 1, Issue 1 pp. 15-30.

*Primary Examiner* — Samira Jean-Louis
(74) *Attorney, Agent, or Firm* — Perkins Coie LLP; Viola T. Kung

(57) ABSTRACT

The present invention provides a pharmaceutical composition for delivering an active agent taxane through transmucosal administration, more particularly through the buccal mucosa or sublingual mucosa. The present invention provides a method for treating cancer by buccal or sublingual administration of the pharmaceutical composition to a subject. The pharmaceutical composition comprises a taxane, a non-ionic surfactant, a viscosity enhancing agent, an adhesive agent, and an alcohol solvent at pH 4-6.

19 Claims, 1 Drawing Sheet

TRANSMUCOSAL TAXANE COMPOSITION

This application is a continuation of U.S. application Ser. No. 13/604,487, filed Sep. 5, 2012. The contents of the above-identified application is incorporated herein by reference in its entirety.

FIELD OF INVENTION

The present invention relates to a method for buccally or sublingually administering to a subject a taxane, which provides an effective treatment of ovarian cancer, breast cancer, lung cancer, prostate cancer, or gastric cancer. The present invention also provides a pharmaceutical composition comprising a taxane, a non-ionic surfactant, a viscosity enhancing agent, an adhesive agent, and an alcohol solvent, at pH 4-6; such pharmaceutical composition is suitable for buccal or sublingual administration.

BACKGROUND OF THE INVENTION

Taxanes are one of the important classes of cancer chemotherapeutic agents. Representatives of taxanes include docetaxel, paclitaxel, cabazitaxel, larotaxel, abraxane, paclitaxel pro-drugs, paclitaxel lipid conjugates, paclitaxel polymer conjugates and the like.

Paclitaxel has been approved for clinical use in the treatment of first line and advanced ovarian cancer in the United States and has been approved for treatment of breast cancer, non small cell lung cancer and AIDS related Kaposi's Sarcoma. Paclitaxel is only slightly soluble in water and this has created significant problems in developing suitable injectable and infusion formulations useful for anticancer chemotherapy. Some formulations of paclitaxel for IV infusion have been developed utilizing CREMOPHOR® EL (polyoxyl castor oil) as the drug carrier because of paclitaxel's aqueous insolubility. However, when administered intravenously, CREMOPHOR® EL is itself toxic and produces vasodilation, labored breathing, lethargy, hypotension and death in dogs. (Rowinsky et al, *J. Natl. Cancer Inst.* 82:1247-1259 (1990))

Docetaxel (N-debenzoyl-N-tert-butoxycarbonyl-10-deacetyl paclitaxel) is commercially available as TAXOTERE® (Rhone-Poulenc Rorer) in a parenteral form. Docetaxel demonstrates a significant antitumour activity against various human malignancies, and is approved for treating patients with locally advanced or metastatic breast cancer, non-small-cell lung cancer, hormone refractory prostate cancer and advanced gastric cancer.

TAXOTERE® contains 40 mg/ml docetaxel and 1040 mg/ml polysorbate 80; it requires a first dilution with 13% ethanol before a further dilution in an intravenous infusion solution. Early in the clinical development of docetaxel, it became clear that docetaxel administration is associated with the occurrence of unpredictable (acute) hypersensitivity reactions. The occurrence of hypersensitivity reactions has, in part, been attributed to intrinsic toxic effects of polysorbate 80, and more specifically to oxidation products and oleic acid present in polysorbate 80, which are known to cause histamine release. (Lorenz et al, *Agents Actions*, 12: 64-80 (1982); Bergh et al, *Contact Dermatitis*, 37: 9-18 (1997)) Polysorbate 80 has been reported to increase plasma viscosity and produce changes in erythrocyte morphology; such effects have been suggested to contribute to mechanisms related to docetaxel-mediated cardiovascular side effects. (Mark et al, *Br. J. Pharmacol*, 134: 1207-1214 (2001))

Cabazitaxel is a taxane compound derived from the renewable needle biomass of yew plants. Cabazitaxel works by disrupting the microtubular network, which is essential for mitotic and interphase cellular functions and causes inhibition of cell division and cell death. Cabazitaxel has been shown to inhibit cell division and tumor cell proliferation by binding to and stabilizing tubulin, a protein in the microtubules of cells which provides a skeleton for maintaining cell shape.

Cabazitaxel is marketed as JEVTANA®, which is indicated in combination with prednisone for treating patients with hormone-refractory metastatic prostate cancer previously treated with docetaxel. JEVTANA® is supplied as a kit consisting of (a) a JEVTANA® injection, which contains 60 mg cabazitaxel in 1.5 mL polysorbate 80; and (b) a diluent, containing approximately 5.7 mL 13% (w/v) ethanol. Prior to administration, the JEVTANA® injection must first be mixed with the diluent, which dilutes the amount of cabazitaxel to 10 mg/mL, and then further diluted into a 250 mL PVC-free container of either 0.9% sodium chloride solution or 5% dextrose solution for infusion.

Docetaxel and paclitaxel with their broad anticancer activity, have contributed significantly to the improved treatment of a number of neoplastic diseases. Unfortunately, until now, the achievements obtained with these compounds have been mitigated by clinical limitations such as acquired or intrinsic resistance of tumors, poor CNS activity. Larotaxel is a semi-synthetic taxoid derivative, selected for development on the basis of its spectrum of in vitro and in vivo activity against taxane-resistant and multidrug-resistant tumors. Due to its broad spectrum of activity and with the possible advantages of surpassing some mechanisms of resistance and penetrating into the CNS, currently larotaxel is selected to conduct a clinical trial study.

Commercially available paclitaxel, docetaxel, and cabazitaxel drugs are administered via intravenous routes, requiring intervention by a physician or other health care professional, entailing considerable discomfort and potential local trauma to the patient and even requiring administration in a hospital setting. Many researchers are working on oral delivery of taxanes. However, paclitaxel and docetaxel were reported to have a poor or inconsistent oral bioavailability upon oral administration. To increase the bioavailability, some oral bioavailability-enhancing agent such as cyclosporin A, cyclosporin D, cyclosporin F or ketoconazole were co-administered to a mammalian patient. The enhancing agent was administered orally from 0.5-24 hours prior to the oral administration of one or more doses of the target agent, or substantially simultaneously with the target agent, or both prior to and substantially simultaneously with the target agent. However, this co-administration approach is not convenient for patients.

There exists a need for a method for delivering a taxane drug with improved bioavailability and fewer side effects.

SUMMARY OF THE INVENTION

The present invention is directed to a method for treating cancer in a subject. The method comprises identifying a subject suffering from cancer, and administering to the buccal mucosa or sublingual mucosa of the subject a pharmaceutical formulation comprising an effective amount of a taxane. Preferred taxanes include docetaxel, paclitaxel, cabazitaxel, and larotaxel.

The pharmaceutical formulation suitable for the present method comprises 0.15-10% (w/v) of the taxane, 20-60% (w/v) of a non-ionic surfactant, a viscosity enhancing agent to provide a viscosity of 200-400 CP, 2-30% (w/v) of an adhesive agent, and an alcohol solvent, the pH of the pharmaceutical formulation is 4-6.

DETAILED DESCRIPTION OF THE INVENTION

Figure 1:
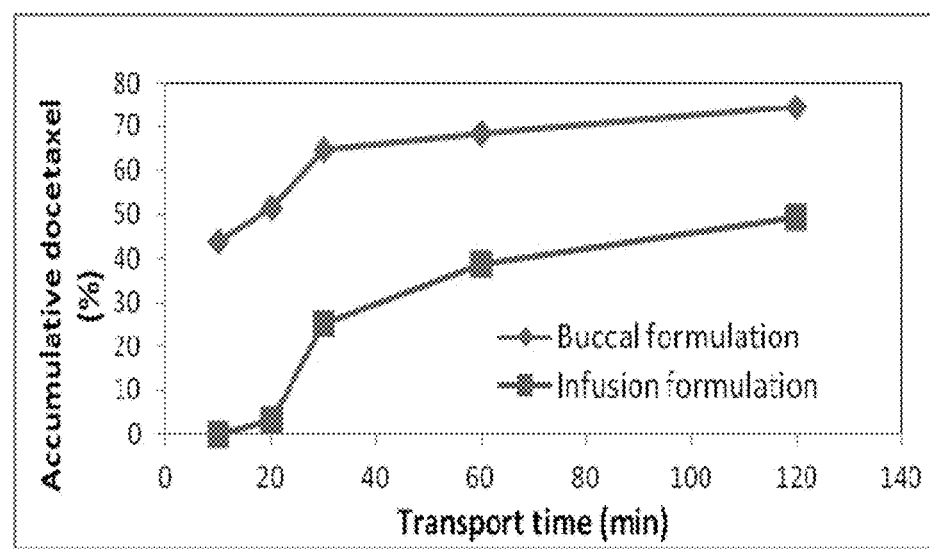
FIG. 1 illustrates the comparison between the buccal docetaxel formulation of the present invention and the commonly used infusion docetaxel formulation in an in vitro permeability experiment using multiple layers of buccal tissue cells.

The inventors have discovered a pharmaceutical composition suitable for buccal or sublingual administration of a taxane such as docetaxel, paclitaxel, cabazitaxel, or larotaxel. The inventors have discovered that when administering such pharmaceutical composition buccally or sublingually to a subject, the taxane is absorbed through the mucous membranes of the mouth, and enter into the bloodstream in minutes. Buccal or sublingual administration of a taxane is advantageous over oral administration because it by passes liver metabolism. Further, taxanes are poorly absorbed from the gastrointestinal tract, thus causing low bioavailability by oral administration.

The current commercial IV infusion taxane formulations such as docetaxel (JEVTANA®), paclitaxel (TAXOL®), and Cabazitaxel (JEVTANA®) are inconvenient to prepare for use; they also cause patient discomfort and side effects. The pharmaceutical composition of the present invention makes it possible to administer taxane topically by a transmembrane route, preferably buccally or sublingually. Buccal epithelium is a relatively permeable non-keratinized tissue; where blood vessels drain directly into the jugular vein. Due to its particular features, buccal mucosa is a preferred site of administration.

The present invention provides a method for treating cancer in a subject by buccal or sublingual administration of a taxane to the subject. The method comprises identifying a subject suffering from cancer, and administering to the buccal mucosa or sublingual mucosa of the subject a pharmaceutical formulation comprising an effective amount of a taxane.

The pharmaceutical composition of the present invention is administered buccally or sublingually by placing the pharmaceutical composition in the mouth of a subject, either under the tongue (sublingual) or between the gum and the cheek (buccal). The pharmaceutical compositions are absorbed through the mucous membranes of the mouth and enter into the bloodstream. Buccal or sublingual administration of the present pharmaceutical composition is effective, because the taxane bypasses the digestive system and is absorbed into the bloodstream in minutes.

The pharmaceutical composition of the present invention is designed for buccal or sublingual administration. The present pharmaceutical composition provides a good solubility of the taxane in the formulation. When the pharmaceutical composition is administered to a subject buccally or sublingually in a single dose or multiple doses daily, a desired plasma taxane level in a subject is maintained for an extended period of time (e.g., at least 8-36 hours), which is at least comparable to those achieved with an IV infusion taxane therapy. The pharmaceutical composition of the present invention is designed to achieve a desired taxane absorption profile and peak blood level and to provide a favorable pharmacokinetic profile.

The pharmaceutical composition of the present invention comprises a taxane, a non-ionic surfactant, a viscosity enhancing agent, an adhesive agent, and an alcohol solvent, the pH of the pharmaceutical composition is 4-6.

"About" when used in this application, refers to ±10% of the recited value.

The taxane (docetaxel, paclitaxel, cabazitaxel, or larotaxel) concentration in the pharmaceutical composition of the present invention in general is about 10 to 160 mg/mL, preferably 15 to 100 mg/mL, or about 20 to 60 mg/mL. The desired amount of taxane in the final formulation will vary depending upon the particular release rate of the taxane.

The solvent suitable for the present pharmaceutical composition is an alcohol. In one embodiment, the solvent is a monohydric alcohol, e.g., ethanol. In another embodiment, the solvent is a polyhydric alcohol, e.g., glycerine, glycerol, or a non-toxic glycol such as polyethylene glycol. Ethanol is a preferred solvent because it is a well accepted and commonly used oral excipient. Ethanol has a high rate of absorption into the buccal membrane and it also acts as a microbial preservative. The amount of the alcohol solvent ranges typically from about 10 to 75% of the composition, more preferably from about 20 to 50%, or 30-40% (w/v). Unless otherwise specified, "%" in this application refers to % w/v.

One or more non-ionic surfactants are used as solubilizing agents to promote a rapid dissolution of docetaxel in the pharmaceutical composition. Suitable non-ionic surfactants include polysorbates (e.g., TWEEN®-80, TWEEN®-20), tyloxapol, polyoxyl castor oil, polaxamers, polyethylene glycol, caprylic triglyceride, polyoxyl stearates (e.g., oxyethylene monostearate), and glyceryl monostearate. A preferred non-ionic surfactant is a polysorbate such as TWEEN®-80. The amount of the non-ionic surfactant in the pharmaceutical composition is at least 20%, for examples, about 20 to 80%, or 30-60%, or 30-50%, or 40% (w/v) of the pharmaceutical composition. When administered by buccal or sublingual route to a subject, the present pharmaceutical composition delivers less amount of a non-ionic surfactant (such as polysorbate or polyoxyl castor oil) systemically to the subject than a commercial infusion formulation, thus minimizing the potential toxicity of the non-ionic surfactant.

A viscosity enhancing agent is included in the pharmaceutical composition to provide a viscosity of about 200-500 CP, preferably 200-400 CP, and more preferably 250-350 CP at 25° C. The viscosity enhancing agent provides an advantage that when the pharmaceutical composition is administered into the buccal cavity of a subject, the risk that the formulation trickles down the patient's throat is minimized or eliminated due to a low degree of circulation of the viscous formulation in the mouth.

Suitable viscosity enhancing agent include glycerol, carrageen, quince seed, gelatin, carboxyl vinyl polymer, hydrogenated starch hydrolysate, maltitol syrup, casein, dextrin, dextran, hydroxyl ethyl cellulose, hydroxypropyl cellulose, a polysaccharide, a pectin, agar, a hydrophilic gum such as acacia gum, guar gum, Arabic gum and xanthan gum, tragacanth gum, alginic acid, a carbomer resin, or a mixture thereof. Preferred viscosity enhancing agents include glycerol, gelatin, carboxy vinyl polymer, sodium hydroxypropyl cellulose, and a gum. Glycerol is especially preferred. The amount of the viscosity agent is about 2-30%, preferably 5-20%, or about 10% (w/v).

One or more adhesive agents are included in the pharmaceutical composition to promote the binding of the active drug to mucosal membranes and to enhance drug absorption and bioavailability. The adhesive agents may be obtained from both natural and synthetic sources. The adhesive agents include polyvinylpyrrolidone (PVP), sodium hyaluronate, acacia gum, alginic acid, carbomers, pectin, and tragacanth. Preferred adhesive agents are polyvinylpyrrolidone (PVP) and sodium hyaluronate. The amount of adhesive agents is about 2-30%, preferably 5-20%, or about 10% (w/v).

As the rate of degradation of taxanes such as docetaxel increases with pH, an acidic pH of the formulation is preferable. A preferred pH of the formulation is about 2-6, more preferably 4 to 6. High pHs such as above 9 are generally avoided as the rate of degradation of docetaxel is increased.

The pH of the formulation may be inherently provided by the excipients present in the formulation; alternatively, a pH adjustment agent may be employed. A pH adjustment agent such as a buffer or a simple acid can be added to the pharmaceutical composition to maintain the pH to 4-6. Suitable acids include organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and mixtures thereof. The amount of a pH adjusting agent is in general 0.1-10% or 0.5-2%.

To increase shelf-life, the formulation may optionally include a microbial preservative. Any preservative which does not adversely interact with the active taxane or any of the excipients may be employed. Preferred preservatives include ethanol, benzyl alcohol, phenol, phenoxyethanol, phenylethyl alcohol, chlorobutanol, benzalkonium chloride, benzethonium chloride, benzoic acid, bronopol, butyl-paraben, cetrimide, chlorhexidine, chlorocresol, cresol, ethylparaben, glycerin, imidurea, methylparaben, phenyl mercuric borate, phenylmercuric nitrate, propylene glycol, propylparaben, sorbic acid, thiomersal, or a mixture thereof. The amount of preservative may range, for example, from about 0.01-10%, or 0.05-2% (w/v).

In addition, or more flavor enhancing agents may be added in the pharmaceutical composition. These can be selected from any of the industry-available natural and synthetically-derived food and pharmaceutical flavors. As non-limiting examples, peppermint, spearmint, wintergreen, cinnamon, menthol and menthone flavors are desirable. A preferred flavor enhancing agent is menthol. The amount of a flavor enhancing agent is about 0.01-3%, or 0.1-2%, or 0.2-1% (w/v).

The pharmaceutical composition of the present invention is administered to the buccal mucosa or sublingual mucosa in the oral cavity of a subject, 1-5 times or 2-3 times a day. The pharmaceutical composition is administered in the form of drops, spray, aerosols, or by any other dosage form. Optionally, the delivering system can be a unit dose or a multiple dose package. The volume of a solution or suspension delivered per dose is about 5 to 1000 μl, preferably about 50-500 μl, or 100-400 Delivery systems for these various dosage forms can be dropper bottles, plastic squeeze units, atomizers, nebulizers, or pharmaceutical aerosols.

The present invention also provides a kit for patients to carry out the present method of treating cancer using buccal or sublingual drug delivery therapy. The kit contains the pharmaceutical formulation to be administered, a container, preferably sealed, for housing the formulation during storage and prior to use, and instructions for carrying out drug administration in an effective manner. The formulation may consist of the drug in unit dosage form. The unit dose is preferably provided in a single-use means of administration, most preferably a dropper.

The present invention is useful in treating a subject that is a mammal, such as humans, dogs and cats. The present invention is particularly useful in treating humans.

The following examples further illustrate the present invention. These examples are intended merely to be illustrative of the present invention and are not to be construed as being limiting.

EXAMPLES

Example 1

Preparation of a Buccal or Sublingual Taxane Formulation 200 mg of an active drug (docetaxel, paclitaxel, cabazitaxel, or larotaxel) is weighed into a 5 mL volumetric flask. 2 g polysorbate 80 is added to the flask and votexed for 3 minutes. Then glycerol (0.5 g), polyvinylpyrrolidone (0.5 g), citric acid (0.05 g), menthol (0.025 g) are added to the flask. Ethanol is then added to make the total volume of 5 mL. The solution is votexed for 5 minutes and mixed well. The final pH is 5.3 (range 5.0-6.0).

The formulation prepared contains the following ingredients in 1 mL ethanol:

active drug (docetaxel, paclitaxel, cabazitaxel and larotaxel), 40 mg (4% w/v);
glycerol (viscosity enhancing agent), 0.1 g (10% w/v);
polysorbate 80 (non-ionic surfactant), 0.4 g (40% w/v);
polyvinylpyrrolidone (adhesive agent), 0.1 g (10% w/v);
citric acid (stabilizing and pH adjuster): 0.01 g (1% w/v); and
menthol (flavour enhancer): 0.005 g (0.5% w/v).

Example 2

In Vitro Uptake and Transport of Docetaxel Using EpiOral (ORL-200) Tissue Model

Materials
Buccal docetaxel formulation: same as Example 1.
Infusion docetaxel formulation: The formulation was prepared according to Taxotere®, (docetaxel injection concentrate), which contains 40 mg anhydrous docetaxel (Xian Natural Field Bio-Technique Co. Ltd, Xian, China) and 1040 mg polysorbate 80 per mL.
Methods
Buccal epithelial tissue (EpiOral ORL-200) as a buccal tissue model was purchased from MatTeck Corporation (Ashland, Mass.). The MatTek assay medium was pre-warmed to 37° C. Using sterile techniques, 0.9 ml of the assay medium was pipetted into each well of sterile 6-well plates. A tissue culture insert containing a buccal membrane tissue was placed into each well of the 6-well plates on top of the pre-warmed assay medium. The 6-well plates containing the tissue samples were then placed into a humidified 37° C., 5% $CO_2$ incubator for 1 hour prior to dosing. 100 μl of the buccal docetaxel formulation solution or 100 μl of the infusion docetaxel formulation was added onto the surface of the buccal tissue in the cell culture insert over the assay medium. After 10, 20, 30, 60, and 120 minutes, 100 µl of the assay medium below the cell culture insert was removed and analyzed for docetaxel concentration by HPLC. Accumulative % of the docetaxel penetration is calculated by comparing the total amount of the docetaxel in the assay medium and the total amount of docetaxel added onto the surface of the buccal membrane.

Results

As shown in FIG. 1, after 10 minutes of incubation, a significant amount (>40%) of docetaxel in the buccal formulation penetrated through the buccal tissue cells, whereas the infusion formulation did not yield any measurable penetration of docetaxel. After 30 minutes of incubation, about 70% of the docetaxel in the buccal formulation penetrated thought the buccal tissue cells, but only about 40% of docetaxel in the infusion penetrated thought the buccal tissue cells The results indicate that the buccal docetaxel formulation of the present invention, when compared with an infusion formulation, significantly enhanced docetaxel delivery through the buccal tissues, with respect to the initiation of transport and the overall transported quantity over time.

Example 3

In Vitro Uptake and Transport of Paclitaxel Using EpiOral (ORL-200) Tissue Model Materials
Buccal paclitaxel formulation: same as Example 1.
Methods Buccal epithelial tissue (EpiOral ORL-200) as a buccal tissue model is purchased from MatTeck Corporation (Ashland, Mass.). The MatTek assay medium is pre-warmed to 37° C. Using sterile techniques, 0.9 ml of the assay medium is pipetted into each well of sterile 6-well plates. A tissue culture insert containing a buccal membrane tissue is placed into each well of the 6-well plates on top of the pre-warmed assay medium. The 6-well plates containing the tissue samples are then placed into a humidified 37° C., 5% $CO_2$ incubator for 1 hour prior to dosing. 100 µl of the buccal paclitaxel formulation solution is added onto the surface of the buccal tissue in the cell culture insert over the assay medium. After 10, 20, 30, 60, and 120 minutes, 100 µl of the assay medium below the cell culture insert is removed and analyzed for paclitaxel concentration by HPLC. Accumulative % of the paclitaxel penetration is calculated by comparing the total amount of the paclitaxel in the assay medium and the total amount of paclitaxel added onto the surface of the buccal membrane.

Results

The results indicate that the buccal paclitaxel formulation of the present invention provides good paclitaxel delivery through the buccal tissues, with respect to the initiation of transport and the overall transported quantity over time.

Example 4

In Vitro Uptake and Transport of Cabazitaxel Using EpiOral (ORL-200) Tissue Model Materials
Buccal cabazitaxel formulation: same as Example 1.
Methods Buccal epithelial tissue (EpiOral ORL-200) as a buccal tissue model is purchased from MatTeck Corporation (Ashland, Mass.). The MatTek assay medium is pre-warmed to 37° C. Using sterile techniques, 0.9 ml of the assay medium is pipetted into each well of sterile 6-well plates. A tissue culture insert containing a buccal membrane tissue is placed into each well of the 6-well plates on top of the pre-warmed assay medium. The 6-well plates containing the tissue samples are then placed into a humidified 37° C., 5% $CO_2$ incubator for 1 hour prior to dosing. 100 µl of the buccal cabazitaxel formulation solution is added onto the surface of the buccal tissue in the cell culture insert over the assay medium. After 10, 20, 30, 60, and 120 minutes, 100 µl of the assay medium below the cell culture insert is removed and analyzed for cabazitaxel concentration by HPLC. Accumulative % of the cabazitaxel penetration is calculated by comparing the total amount of the cabazitaxel in the assay medium and the total amount of cabazitaxel added onto the surface of the buccal membrane.

Results

The results indicate that the buccal cabazitaxel formulation of the present invention provides good cabazitaxel delivery through the buccal tissues, with respect to the initiation of transport and the overall transported quantity over time.

Example 5

In Vitro Uptake and Transport of Larotaxel Using EpiOral (ORL-200) Tissue Model

Materials
Buccal larotaxel formulation: same as Example 1.
Methods

Buccal epithelial tissue (EpiOral ORL-200) as a buccal tissue model is purchased from MatTeck Corporation (Ashland, Mass.). The MatTek assay medium is pre-warmed to 37° C. Using sterile techniques, 0.9 ml of the assay medium is pipetted into each well of sterile 6-well plates. A tissue culture insert containing a buccal membrane tissue is placed into each well of the 6-well plates on top of the pre-warmed assay medium. The 6-well plates containing the tissue samples are then placed into a humidified 37° C., 5% $CO_2$ incubator for 1 hour prior to dosing. 100 µl of the buccal larotaxel formulation solution is added onto the surface of the buccal tissue in the cell culture insert over the assay medium. After 10, 20, 30, 60, and 120 minutes, 100 µl of the assay medium below the cell culture insert is removed and analyzed for larotaxel concentration by HPLC. Accumulative % of the larotaxel penetration is calculated by comparing the total amount of the larotaxel in the assay medium and the total amount of larotaxel added onto the surface of the buccal membrane.

Results

The results indicate that the buccal larotaxel formulation of the present invention provides good larotaxel delivery through the buccal tissues, with respect to the initiation of transport and the overall transported quantity over time.

Example 6

Clinical Evaluation of Buccal Administration of a Docetaxel Formulation

The objective of this experiment is to determine whether docetaxel would be absorbed by buccal mucosa and produce a sustained plasma level.

Materials and Methods

Figure 2:
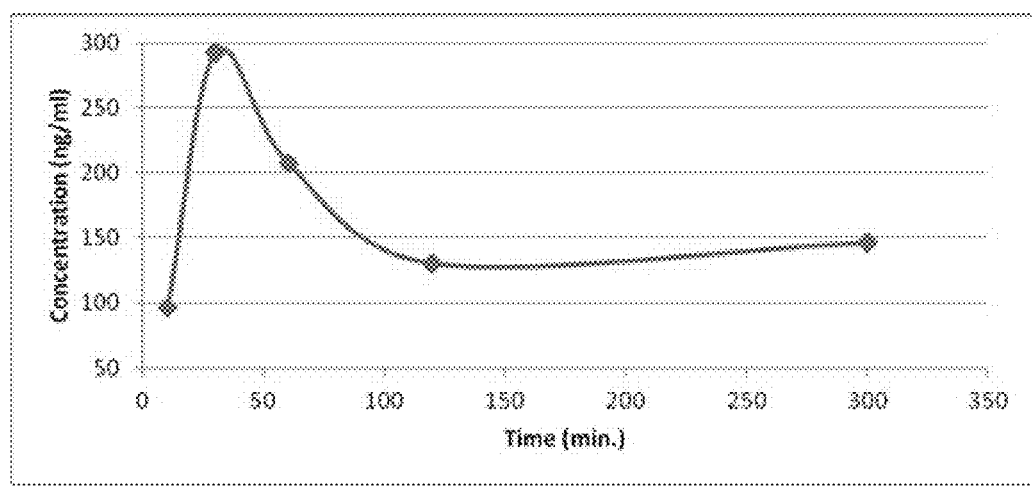
FIG. 2 is a graph reflecting the levels of docetaxel in serum samples taken over a period of 5 hours from a human subject following buccal administration of the docetaxel formulation of the present invention.

The liquid formulation of Example 1 was prepared for administration in a syringe. 0.1 mL of the formulation (containing 4 mg docetaxel) was evenly dropped over the subject buccal mucosa of a human subject. The subject was instructed not to swallow for as long as possible. Blood samples were drawn from the individual at time intervals of 15, 30, 60, 120, and 300 minutes after the docetaxel dose. Serum was separated from each whole blood sample by centrifugation at 2000 rpm in a 25 centimeter rotor. Docetaxel concentrations of the samples were determined using HPLC coupled with a tandem mass spectrometer (LC/MS/MS) running mono reaction monitoring (MRM) at a transaction pair of 808/526. FIG. 2 is the plot of the docetaxel levels in serum samples against sampling time.

Results

The pharmicokinetic profile shown in FIG. 2 was observed in a human subject after a single 4 mg dose in 100 µL using the formulation described in example 1. As shown in FIG. 2, the plasma level of docetaxel administered buccally reached a maximum concentration (Cmax) of about 0.35 µM at about 30 minutes, followed by a reduction in concentration. The plasma level of docetaxel remained at a concentration above 100 ng/mL over 5 hours. The results indicate that buccal administration of the present pharmaceutical composition is practical for generating a pharmacokinetic profile similar to that from i.v. infusion, which has been shown to be safe and efficacious.

Example 7

Comparison of the Stability of the Buccal Formulation with the Infusion Formulation Materials and Methods Stability experiments were conducted on the buccal formulation of the present invention (Example 1) in parallel with the infusion formulation Taxotere® (Example 2) currently available in clinic practice. The samples were storage at (a) 25° C. with 60% relative humidity (RH) and (b) 40° C. with 75% relative humidity (RH) for two weeks. The stability results as determined by HPLC with UV detection are provided in Table 1.

Results

At time zero, both buccal formulation and infusion formulation had similar impurity profiles. Three major degradation products were identified using this HPLC method. Impurity A, 10-oxo-docetaxel, is a docetaxel degradation product comprising an oxo formation at the C10 position. Impurity B, 7-hydroxy-epi-docetaxel, is a docetaxel degradation product comprising epimerization at the C7 position. Impurity C, 7-epi-10-oxo-docetaxel, is a docetaxel degradation product comprising both epimerization at the C7 position followed by an oxo formation at the C10 position.

After 6 months of incubating at 25° C./60% RH, docetaxel in the infusion formulation had a significant degradation and only 77% of the added docetaxel remained. However, docetaxel in the buccal formulation showed good stability with about 92% remaining unchanged.

Under the accelerated condition at 40° C./75% RH, the infusion formulation degraded much faster. After two weeks, 68% of docetaxel remained in the infusion formulation, while the buccal formulation retained more than 92% unchanged docetaxel.

By analyzing the degradation results, it is concluded that the ingredients in the buccal formulation effectively prevented docetaxel from oxidation. After incubation at both temperatures, the oxidation products oxo-docetaxel and 7-epi-oxo-docetaxel found in the buccal formulation were significantly lower than that in the infusion formulation.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications can be made therein without departing from the scope of the present invention as set forth in the claims. To particularly point out and distinctly claim the subject matter regarded as invention, the following claims conclude this specification.

What is claimed is:

1. A pharmaceutical formulation for buccal or sublingual administration comprising 0.15-10% (w/v) of a taxane, 20-60% (w/v) of a non-ionic surfactant, a viscosity enhancing agent to provide a viscosity of 200-400 CP, 2-30% (w/v) of an adhesive agent, and 10-75% (w/v) of ethanol, wherein the pH of the pharmaceutical formulation is 4-6, and the taxane is selected from the group consisting of docetaxel, paclitaxel, cabazitaxel, and larotaxel.

2. The pharmaceutical formulation according to claim 1, wherein said non-ionic surfactant is polysorbates, tyloxapol, polyoxyl castor oil, polaxamers, polyethylene glycol, caprylic triglyceride, polyoxyl stearates, or glyceryl monostearate.

TABLE 1

Stability study on a buccal formulation and an infusion formulation

| Stability storage condition | Test Time | Formulation | Purity (% area) | Impurity-10-oxo-DCT | Impurity-7-epi-DCT | Impurity-7-epi-10-oxo-DCT | Total unknown |
|---|---|---|---|---|---|---|---|
| 25° C./60% RH | Initial | Infusion formulation | 93.55 | 0.73 | 2.65 | 2.61 | 0.47 |
| | | Buccal formulation | 93.51 | 0.76 | 2.64 | 2.62 | 0.47 |
| | 6 months | Infusion formulation | 77.22 | 4.91 | 3.71 | 10.29 | 3.87 |
| | | Buccal formulation | 91.62 | 0.83 | 3.21 | 3.34 | 1.00 |
| 40° C./75% RH | 2 weeks | Infusion formulation | 68.15 | 4.12 | 4.93 | 16.26 | 6.53 |
| | | Buccal formulation | 92.12 | ND | 3.33 | 3.33 | 1.22 |

3. The pharmaceutical formulation according to claim 2, wherein said non-ionic surfactant is polysorbate.

4. The pharmaceutical formulation according to claim 2, wherein the non-ionic surfactant is polyoxyl castor oil.

5. The pharmaceutical formulation according to claim 1, wherein said viscosity enhancing agent is glycerol, sodium hydroxypropyl cellulose, gelatin, carboxy vinyl polymer, polyvinylpyrrolidone, or a gum, in an amount of 2-30% (w/v).

6. The pharmaceutical formulation according to claim 5, wherein said viscosity enhancing agent is glycerol.

7. The pharmaceutical formulation according to claim 1, wherein said adhesive agent is polyvinylpyrrolidone, acacia gum, alginic acid, carbomers, pectin, or tragacanth.

8. The pharmaceutical formulation according to claim 7, wherein said adhesive agent is polyvinylpyrrolidone.

9. The pharmaceutical formulation according to claim 1, further comprising a flavor enhancing agent selected from the group consisting of menthol, menthone, peppermint, spearmint, wintergreen, and cinnamon.

10. The pharmaceutical formulation according to claim 9, wherein said flavor enhancing agent is menthol.

11. The pharmaceutical formulation according to claim 1, further comprising an anti-bacteria preservative.

12. The pharmaceutical formulation according to claim 1, in a form of liquid, spray, or aerosol.

13. The pharmaceutical formulation according to claim 1, wherein the non-ionic surfactant is polysorbate, the viscosity enhancing agent is glycerol, and the adhesive agent is polyvinylpyrrolidone.

14. The pharmaceutical formulation according to claim 13, wherein the pharmaceutical formulation further comprises 0.1-2% (w/v) of menthol.

15. The pharmaceutical formulation according to claim 1, wherein the taxane is docetaxel.

16. The pharmaceutical formulation according to claim 13, wherein the taxane is docetaxel.

17. The pharmaceutical formulation according to claim 1, wherein the taxane is paclitaxel.

18. The pharmaceutical formulation according to claim 13, wherein the taxane is paclitaxel.

19. The pharmaceutical formulation according to claim 1, wherein the pharmaceutical formulation comprises 20-50% (w/v) of ethanol.

* * * * *